United States Patent
Lin

[11] Patent Number: 5,196,014
[45] Date of Patent: Mar. 23, 1993

[54] VERTEBRAL LOCKING AND RETRIEVING SYSTEM

[76] Inventor: Chih-I Lin, 513 S. Golden Pardos Dr., Diamond Bar, Calif. 10765

[21] Appl. No.: 924,448

[22] Filed: Aug. 4, 1992

Related U.S. Application Data
[63] Continuation-in-part of Ser. No. 764,222, Sep. 23, 1991.

[51] Int. Cl.$^5$ .............................................. A61B 17/00
[52] U.S. Cl. ...................................... 606/61; 606/60; 606/64; 606/72
[58] Field of Search ................. 606/53, 54, 55, 57, 606/59, 60, 61, 72, 73, 86, 87, 90, 105

[56] References Cited
U.S. PATENT DOCUMENTS

| | | | |
|---|---|---|---|
| 3,997,138 | 12/1976 | Crock et al. | 606/61 X |
| 4,611,580 | 9/1986 | Wu | 606/73 X |
| 4,854,304 | 8/1989 | Zielke | 606/61 |
| 4,988,349 | 1/1991 | Pennig | 606/57 X |
| 5,030,220 | 7/1991 | Howland | 606/61 |
| 5,042,982 | 8/1991 | Harms et al. | 606/61 |

FOREIGN PATENT DOCUMENTS
9111967 4/1991 World Int. Prop. O. ............ 606/59

Primary Examiner—Robert A. Hafer
Assistant Examiner—Sam Rimell
Attorney, Agent, or Firm—Bacon & Thomas

[57] ABSTRACT

A vertebral locking and retrieving system comprises at least one locking pin assembly, a coupling component, a remedial component, and a plurality of securing components. The locking pin assembly is composed of a threaded pin, a receiving mount and a bolt for fastening the threaded pin and the receivng mount together wherein the threaded pin and the receiving mount form therebetween a specified angle. The coupling component is connected at one end thereof to the receiving mount of the locking pin assembly. The remedial component is secured at one end thereof to the deformed vertebra or to the upper vertebra or the lower vertebra immediately adjacent to the deformed vertebra and is connected at another end thereof to another end of the coupling component. The securing components are provided to fixedly fasten the locking pin assembly and the remedial component with the coupling component.

10 Claims, 4 Drawing Sheets

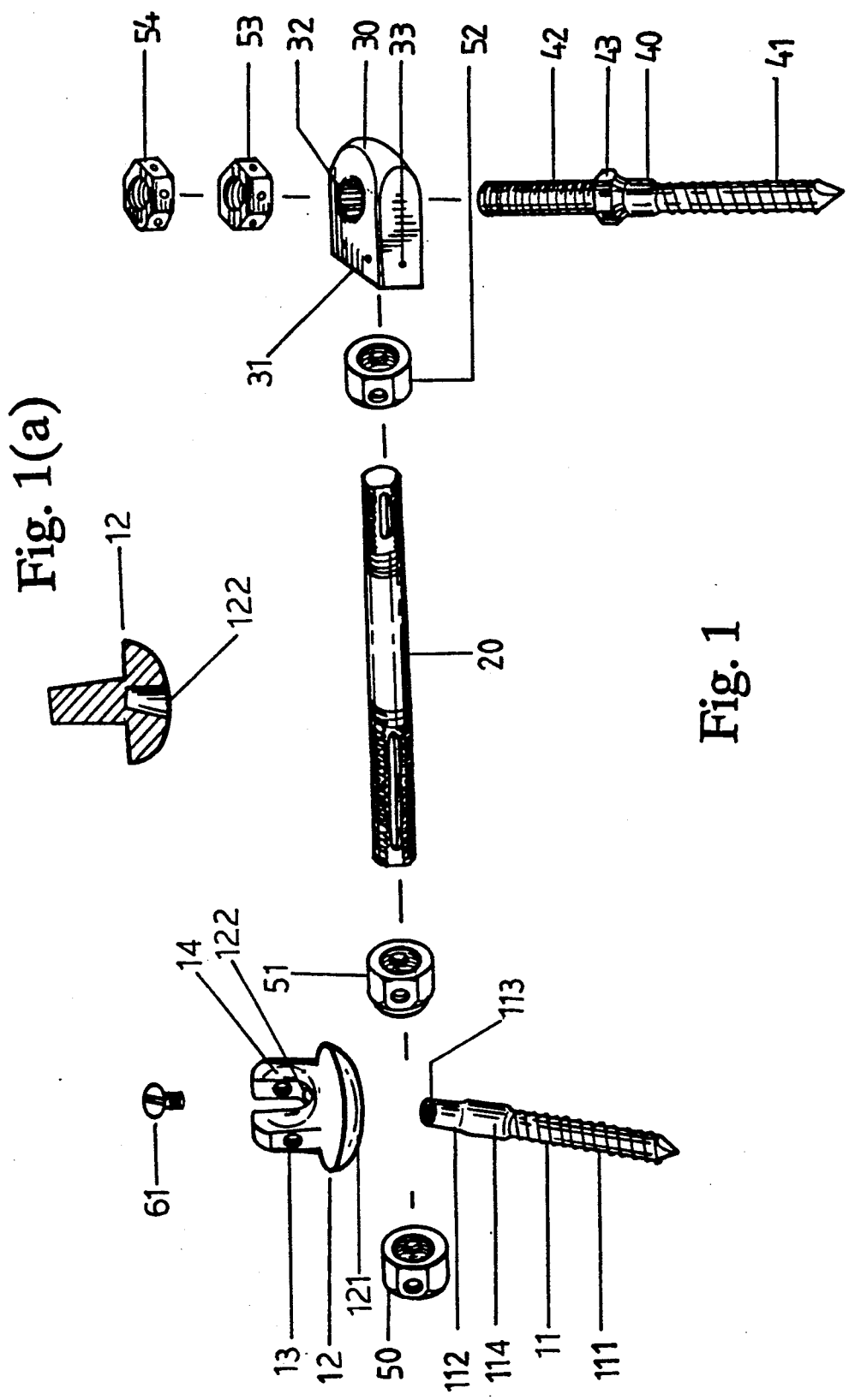

VERTEBRAL LOCKING AND RETRIEVING SYSTEM

This is a continuation in part of U.S. application Ser. No. 07/764,222 filed Sep. 23, 1991.

BACKGROUND OF THE INVENTION

1. Field of the Invention

The present invention relates to a vertebral locking and retrieving system.

2. Description of the Prior Art

In general, conventional vertebral locking and retrieving systems of the prior art involve a locking process of multiple vertebrae, as exemplified by the LUGUE rod and the HARRINGTON rod, both made by Zimmer Company of U.S.A., and the ROY-CAMILLE plate produced by Howmedia Corporation of U.S.A. Such known prior art arrangements require a surgeon to make a long incision, which generally takes up too much of a surgeon's time and may bring about excessive bleeding by a patient receiving the treatment. The case in point is the LUGUE rod, which must be secured to two upper and lower vertebrae immediately adjacent to the injured or the deformed vertebra. This means that a surgeon is required to make a large incision to fix at least five segments of the spinal column. As a result, the patient's ability to move about is greatly hampered in the wake of such a surgical operation. In addition, the pressure exerting on the patient's nervous system by the locking and retrieving system of the prior art can not be effectively mitigated in view of the facts that the locking process is confined to a rear plate and that the retrieval of a front plate is not possible.

Furthermore, the surgical implantation of the conventional vertebral locking and retrieving systems of the prior art is further complicated by the fact that seven cervical vertebrae, twelve thoracic vertebrae, five lumbar vertebrae, and one caudal vertebra of the human spinal column differ in curvatures.

Other types of prior art vertebral locking and retrieving systems are disclosed respectively in U.S. Pat. Nos. 4,611,581 and 4,696,290. Such systems have also failed to deal with the surgical problems described above. In short, the existing vertebral locking and retrieving systems of the prior art have failed to address the surgical problems that are derived mainly from the fact that the curvatures of various vertebrae of the human spinal column are different from one another.

It is therefore the primary object of the present invention to provide a vertebral locking and retrieving system with locking pin assemblies which are designed in such unique manners that they have specific angles permitting the locking pin assemblies to cooperate with the specific curvatures of various vertebrae and that they serve to overcome the problems during and after the surgical operation having to do with locking multiple vertebrae.

It is another object of the present invention to provide a vertebral locking and retrieving system with means which can be used to lock two vertebrae of the spinal column.

It is still another object of the present invention to provide a vertebral locking and retrieving system with locking pin assemblies designed to have specific angles for correcting the position of various vertebrae having different curvatures.

SUMMARY OF THE INVENTION

In order to achieve the objects of the present invention, a vertebral locking and retrieving system comprising a locking pin assembly, a coupling component, a remedial component, and a plurality of securing components is disclosed. The locking pin assembly includes a threaded pin, a receiving mount and a fastening bolt. The threaded pin defines a longitudinal axis and has a threaded portion at one end thereof adapted to be secured to a normal, healthy vertebra and a threaded bore being formed axially at the other end thereof. The receiving mount has a hole adapted to receive the other end of the threaded pin. The fastening bolt is adapted to be threaded into the threaded bore of the threaded pin via the hole of said receiving mount such that the receiving mount is fastened to the threaded pin at an acute angle of deflection relative to the axis defined by the threaded pin. The coupling component is connected at one end thereof to the receiving mount of the locking pin assembly. The remedial component is secured at one end thereof to a deformed vertebra immediately adjacent to the healthy vertebra to which the locking pin assembly is secured or a vertebra next to the deformed vertebra and different from this healthy vertebra and is connected at its other end thereof to the other end of the coupling component. The securing components enable the locking pin assembly and the remedial component to be fixedly secured to the coupling component.

The receiving mount of the locking pin assembly in the preferred embodiments of the present invention takes the form of a fork, preferably a horseshoe-type structure, or a ring-type structure, and the hole of the receiving mount is provided at a portion between both arms of the horseshoe-type fork. Additional threaded holes, preferably two threaded holes, may be provided on both arms of the receiving fork so as to reinforce the connection between the locking pin assembly and the coupling component by tightening screws into the threaded holes and against the coupling component.

The remedial component of the present invention may be a conventional screw, a laminar hook, or a locking pin with a specified angle. A plurality of remedial components may be used in combination with one coupling component of the present invention depending on the position and the symptom of the deformed vertebra and the surgical requirements.

In the preferred arrangement, the coupling components used in the present invention may include a single threaded rod or a plurality of threaded rods joined as a one-piece component by blocks having threaded bores into which the rods are received.

The foregoing features, objectives and advantages of the present invention will be better understood by studying the following detailed description of the preferred embodiments, in conjunction with the drawings provided herein.

BRIEF DESCRIPTION OF THE DRAWINGS

FIG. 1 shows an exploded perspective view illustrating a vertebral locking and retrieving system constructed according to one of the preferred embodiments of the present invention.

FIG. 1(a) is a longitudinal vertical sectional view of the horseshoe-type fork 12 of the vertebral locking and retrieving system of FIG. 1.

DETAILED DESCRIPTION OF THE PREFERRED EMBODIMENTS

Figure 2A:
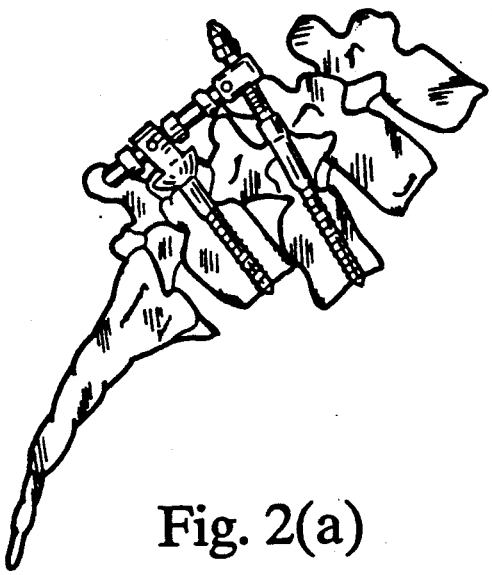
FIG. 2(a)-2(c) show a series of correction procedures of a deformed vertebra by means of the vertebral locking and retrieving system shown in FIG. 1.

In general, the vertebral locking and retrieving system of the present invention can be made of orthopedic materials, such as the iron-based stainless steel 316LVM, the titanium-based material Ti-6-4, and an alloy of chromium, molybdenum and cobalt. The number of locking pin assemblies used is of course dependent on the surgical requirements. The locking pin assembly of the present invention is characterized in that its receiving mount and its threaded pin form a specified angle, such as 180°, 175°, 170°, or 165°, with a respective deflection plane angle being 0°, 5°, 10°, 15°, so as to meet the angular requirements of various vertebrae. Furthermore, with the employment of different combination of locking pin assemblies having the above-mentioned deflection plane angles of 0°, 5°, 10°, 15°, a slipped vertebrae can be properly retrieved to have an appropriate angle consistent with normal human anatomy, such as 0°, 5°, 10°,15°, 20° (5°+15°), 25° (10°+15°), and 30° (15°+15°). This is something beyond the reach of the prior art systems. In addition, working with the prior art system, a surgeon would have to depend entirely on his or her own judgement and clinical experiences to determine the locking angle of the deformed vertebra. On the other hand, the present invention permits a surgeon to study in advance, before operating on the patient, the X-ray negatives with regard to the locking angles of the patient's vertebrae so as to select the most suitable locking pin assembly to use.

Moreover, the receiving mount and the threaded pin of the locking pin assembly are two separated components such that the receiving mount can be fastened to the threaded pin after the threaded pin being secured to a vertebra, and thus permits the surgeon to have a chance to amend the locking angle by choosing a receiving mount having a different deflection angle if the threaded pin secured to the vertebra should deflect from its planned angle.

Referring to FIGS. 1 and 1(a), the vertebral locking and retrieving system embodied in the present invention is shown comprising mainly a locking pin assembly (11, 12, 61), a threaded rod 20, a block 30, a remedial screw 40, and a plurality of nuts 50, 51, 52, 53, and 54.

The locking pin assembly is composed of a threaded pin 11, a receiving horseshoe-type fork 12, and a bolt 61. The threaded pin 11 has a threaded portion 111 at its lower end which is used to lock the normal vertebra immediately adjacent to the deformed vertebra under treatment, a tapered cylinder 112 at its upper end having a threaded bore 113 which is formed axially at the center thereof, and a stop protrusion 114 located between the two ends. The receiving horseshoe-type fork 12 has a recess 14 on each lateral side thereof, a hole 122 located at the lower portion and at a position between both arms of the horseshoe-type fork 12, a flange 121 protruding outwardly at the lower portion and surrounding the hole 112 thereof, and screw holes 13 on the two arms of the horseshoe-type fork 12. As shown in FIG. 1(a), the hole 122 is formed at an acute angle of deflection relative to the plane defined by the two arms of the horseshoe-type fork 12, and gradually narrower towards the upper end of the fork 12 in corresponding to the tapered end 112 of the threaded pin 11. Alternatively, the tapered end 112 of the threaded pin 11 has a polygonal transverse section and the hole 122 of the horseshoe-type fork 12 has a corresponding polygonal shape. The horseshoe-type fork 12 is able to be fastened to the threaded pin 11 by inserting the tapered end 112 of the threaded pin 11 into the hole 122 and threading the bolt 61 from the top of the hole 122 into the threaded bore 113 of the threaded pin 11.

The block 30 is provided with a through hole 32, a plurality of small threaded holes 33, and a large threaded bore 31 used to engage with the threaded rod 20. The remedial screw 40 comprises a screw end 41 intended to be secured to the deformed vertebra, a threaded end 42 to be placed through the through hole 32 of the block 30, and a stopping protrusion 43, located between the screw end 41 and the threaded end 42, intended for use in stopping the block 30. The remedial screw 40 and the block 30 are components serving to correct and restore the deformed vertebra as will be discussed more fully below.

The nuts 50 and 51 are used to fixedly attach the locking pin assembly to threaded rod 20, wherein the nuts 50, 51 are mounted on the screw rod 20 and threaded into recesses 14 of fork 12 separately when screw rod 20 extends through the slot defined by the horseshoe shape of fork 12. The block 30 and the remedial screw 40 are fastened securely by means of nuts 53 and 54. If necessary, additional reinforcing screws (not shown) may be provided to secure the engagement between the locking pin assembly and threaded rod 20 by tightening the reinforcing screws into screw holes 13 of the locking pin assembly and against the threaded rod 20.

Figure 2B:
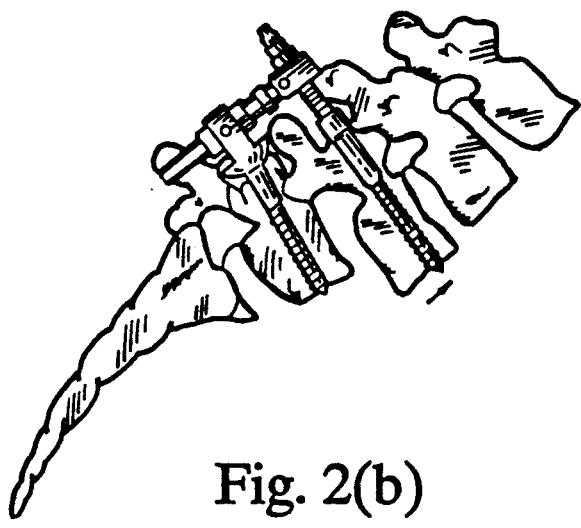
Figure 2C:
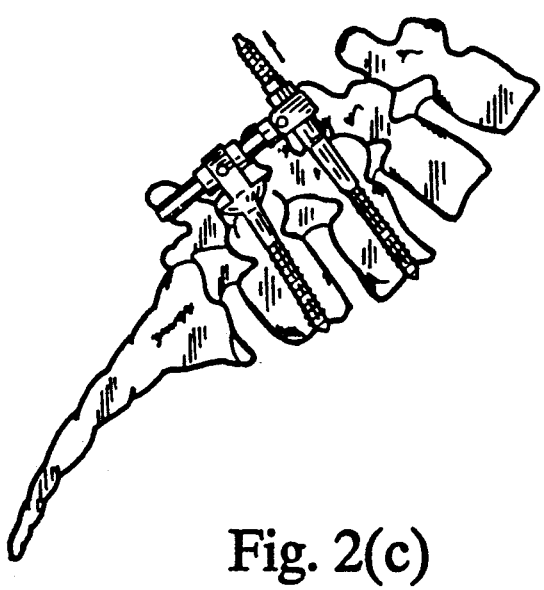

Now referring to FIG. 2(a), the fourth segment of the lumbar vetebrae is shown slipping from a normal, desired position prior to tightening of nuts 50 and 51 into the recesses 14 of locking pin assembly. However, the slipped segment of the lumber vertebrae is restored to its desired position of curvature relative to other normal and healthy segments of the lumber vertebrae as a result of the tightening action of nuts 50 and 51, as shown in FIG. 2(b). This is possible because the locking pin assembly is designed with a specified curvature (as discussed above) permitting the locking pin assembly to negotiate and cooperate with a give segment of the lumber vertebrae. Now, as shown in FIG. 2(c), the nut 52 has been tightened against block 30 so as to restore a normal clearance between the slipped vertebra and the rest of the normal and healthy segments of the lumbar vertebra. As nuts 53 and 54 are screwed respectively into their appropriate positions (i.e. from the FIG. 2(b) position to the FIG. 2(c) position), the slipped vertebra of the lumber vertebrae is retrieved to its normal position.

Figure 3:
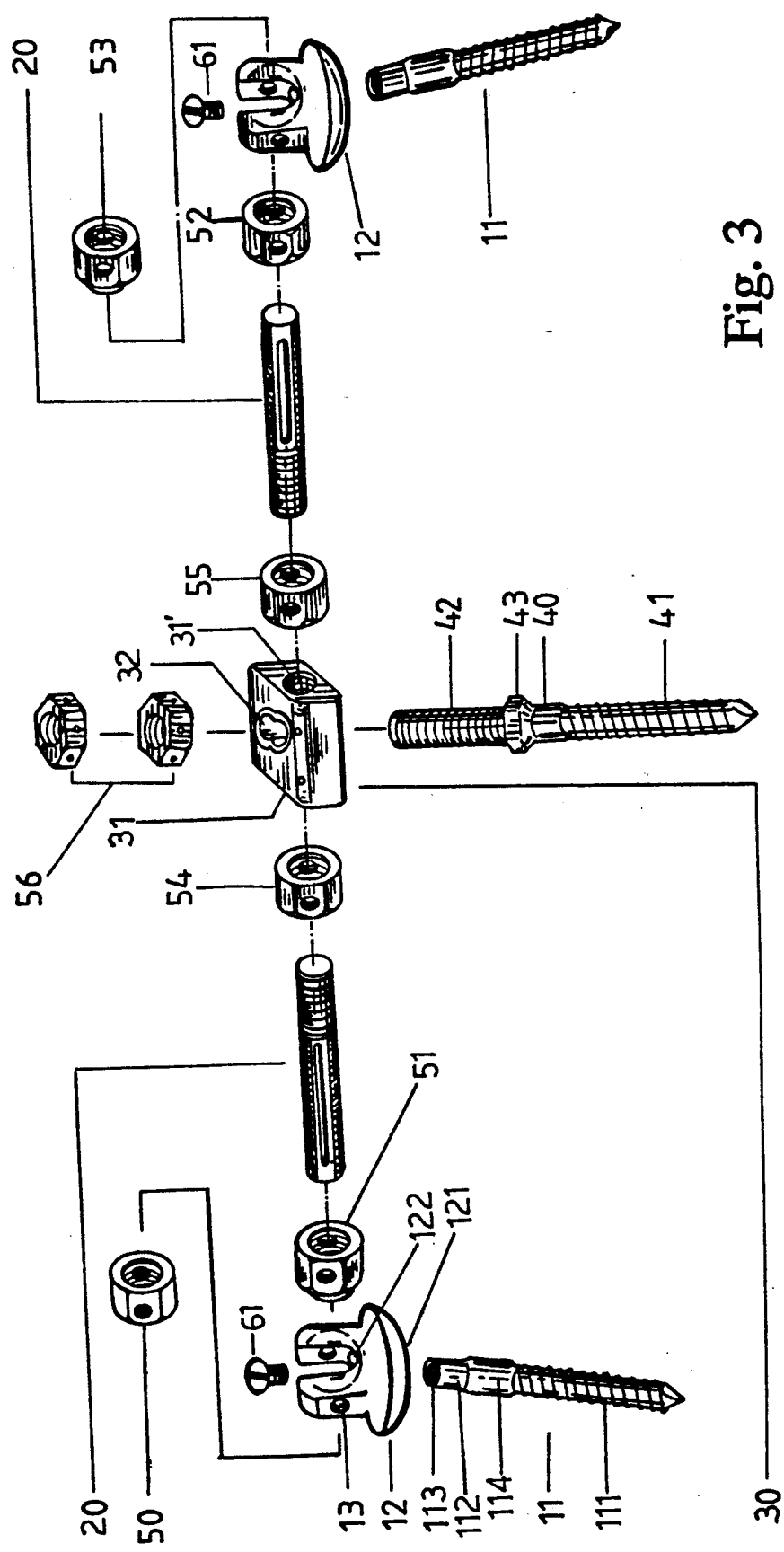
FIG. 3 shows an exploded perspective view of a vertebral locking and retrieving system constructed according to another preferred embodiment of the present invention.

Another preferred embodiment of the present invention is illustrated in FIG. 3 wherein like numerals are used to designate elements corresponding to the above described embodiment. The locking pin assembly, which is composed of a threaded pin 11, a receiving fork 12, and a bolt 61, is again used to secure the vertebrae immediately adjacent to the deformed vertebra. A connecting block 3 is provided with an 8-shape through hole 32 and threaded bores 31 and 31'. Threaded rods 20 are threadably received within respective threaded bores 31 and 31' of block 30. The remedial screw 40 is intended to remedy the deformed vertebra and is similar in structure to the one shown in FIG. 1. In this embodiment, however, two locking pin assemblies and two threaded rods 20 are fastened together to form a unitary body by means of nuts 50, 51, 52, and 53. The two threaded rods 20 and the connecting block 30 are fixedly secured together by threading nuts 54 and 55 against the block 30. In the meantime, the nuts 56 are used to couple the block 30 with the remedial screw 40 with the 8-shaped through hole 32 permitting a slight adjustment of remedial screw 40 relative to the axis defined by threaded rods 20. The fastening block 30 and/or the threaded rods 20 can be constructed with a specific angle for enabling the system to cooperate with the curvature of the deformed vertebra.

Figure 4C:
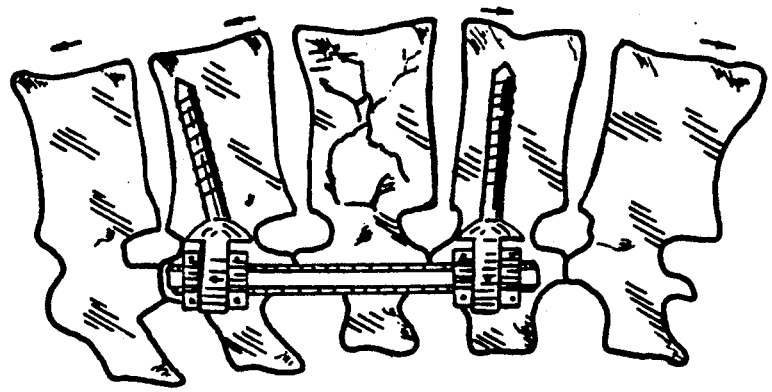
FIG. 4(a)-4(c) show a series of correcting procedures of a deformed vertebra by means of a third preferred embodiment of the present invention.
Figure 4B:
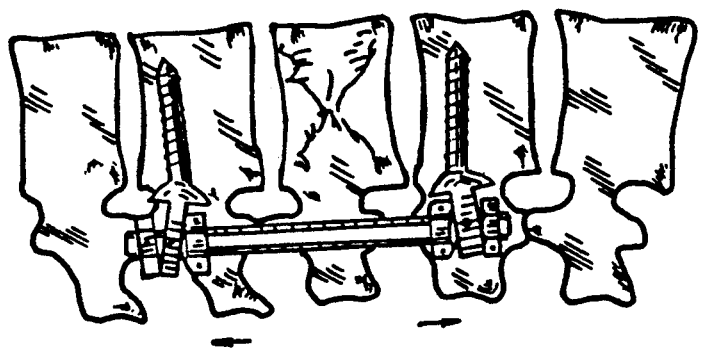
Figure 4A:
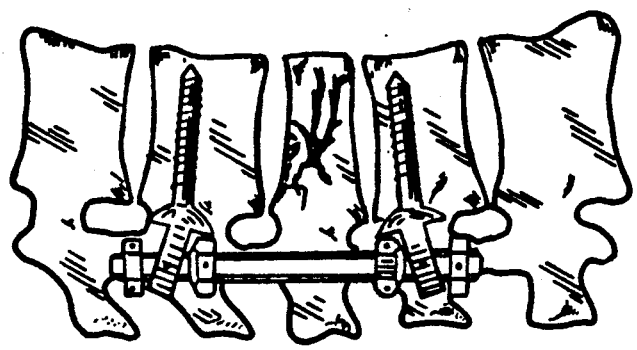

Now referring to FIGS. 4(a), 4(b), 4(c), a third embodiment of the present invention is shown comprising two locking pin assemblies, one threaded rod as the coupling component and two sets of nuts. These components have not been labeled in FIGS. 4(a)–4(c), however, it should be clear that the structure is directly analogous to the connection of locking pin assemblies to their respective threaded rods 20 in the prior embodiments described. One of the locking pin assembly is used to serve as a remedial component and is secured to the upper or the lower vertebra immediately adjacent to the deformed vertebra. In FIG. 4(a), the deformed vertebra is shown along with the present locking and retrieving embodiment implanted but which has not been securely fastened. In FIG. 4(b), the locking pin assemblies are secured to appropriate positions on the threaded rod as a result of tightening actions of two sets of nuts. Therefore, a locking pin assembly with a specified angle is able to work to lock and retrieve the deformed vertebra. Upon completion of such treatment, all vertebrae in question have been restored to their respective normal positions, as shown in FIG. 4(c).

Based on the above discussion, it can readily be seen that the vertebral locking and retrieving system of the present invention is characterized in that it comprises locking pin assemblies, threaded rods, and nuts, all of which can be selectively employed in accordance with the position of the deformed vertebra, the symptoms of the deformed vertebra and the surgical requirements. For example, if the deformed vertebra happens to be the fourth vertebra of the lumbar vertebrae, the vertebral locking and retrieving system of the present invention shown in FIG. 1 functions effectively. In such a case, one threaded rod with the connecting block serves as the coupling component while a threaded screw is used as the remedial component. In addition, a plurality of nuts are used to work as locking components (see FIG. 1 and its corresponding text). In treating some slipped lumbar vertebrae, two threaded rods united by one connecting block are used as the coupling component for two locking pin assemblies and one threaded screw as in the FIG. 3 embodiment. In the case of vertebral fracture or camel back, one threaded rod may be used to serve as the coupling component to interconnect two locking pin assemblies, one of which is used to work as a remedial component (see FIGS. 4(a), 4(b), 4(c), and the corresponding text). Moreover, the locking pin assembly used in these surgical operation permits the surgeon to have a chance to amend the locking angle by choosing a receiving mount having a different deflection angle if the threaded pin secured to the vertebra should deflect from its planned angle.

In order to achieve a better surgical treatment, the present invention can also be employed in conjunction with numerous bone reinforcing devices known in the prior art, such as a cross bridging system.

From the above description, it can readily be seen that the present invention is characterized in that it comprises at least one locking pin assemblies which is designed with a specified angle enabling the locking pin assembly to cooperate with the specific curvature of the deformed vertebra under treatment, and that its various components can be used in different combinations on the basis of the surgical requirements and the symptom of the deformed vertebra under treatment. Furthermore, the present invention serves to simplify the surgical operation in such ways that it does not require of a surgeon to make a large incision, thereby minimizing the risk of an excessive bleeding by the patient receiving treatment; the patient's ability to move about is not seriously compromised by the surgical operation; and the patient's nervous system is less vulnerable to the pressure exerted thereon by the implanted system.

The embodiments of the present invention described above are to be considered in all respects as merely illustrations of principles of the present invention. Accordingly, the present invention is to be limited only by the scope of the following claims.

I claim:

1. A vertebral locking and retrieving system for use in retrieving a deformed vertebra and maintaining the deformed vertebra in a normal, healthy position comprising:

at least one locking pin assembly having a threaded pin; a receiving mount and a fastening bolt; said threaded pin defining a longitudinal axis and having a threaded portion at one end thereof adapted to be secured to a normal, healthy vertebra and a threaded bore being formed axially at the other end thereof; said receiving mount having a hole adapted to receive the other end of said threaded pin; said fastening bolt having a head which has a diameter larger than that of the hole of said receiving mount adapted to be threaded into the threaded bore of said threaded pin through the hole of said receiving mount such that said receiving mount is fastened to said threaded pin at an acute angle of deflection relative to the axis defined by said threaded pin;

a remedial component adapted to be secured at one end thereof to one of a deformed vertebra located immediately adjacent to said normal, healthy vertebra or to a vertebra immediately adjacent to the deformed vertebra but different from said normal, healthy vertebra to which said at least one locking pin assembly is secured;

coupling means for interconnecting said at least one locking pin assembly and said remedial component; and fastening means for fixedly securing said at least one locking pin and said remedial component to said coupling means.

2. A vertebral locking and retrieving system as claimed in claim 1, wherein said coupling means includes a rod having first and second threaded ends.

3. A vertebral locking and retrieving system as claimed in claim 2, wherein said receiving mount of said at least one locking pin assembly has an horseshoe-shaped structure thereby defining a slot through which said rod extends, and said hole of said receiving mount is provided at a portion between both arms of said horseshoe-shaped structure and connects with said slot.

4. A vertebral locking and retrieving system as claimed in claim 3, wherein said fastening means includes a pair of nuts which are threadably attached to said rod on opposite sides of said receiving mount.

5. A veretral locking and retrieving system as claimed in claim 4, wherein said receiving mount is formed with recesses about opposite lateral sides of said slot, said pair of nuts being tightened into said recesses.

6. A vertebral locking and retrieving system as claimed in claim 1, wherein said one end of said remedial component is threaded and the other end of said remedial component is connected to said coupling means.

7. A vertebral locking and retrieving system as claimed in claim 6, wherein said coupling means includes a rod having first and second threaded ends and a block, said first and second threaded ends of said rod being fixedly secured, by said fastening means, to said receiving mount of said at least one locking pin assembly and said block respectively, the other end of said remedial component being fixedly secured to said block.

8. A vertebral locking and retrieving system as claimed in claim 7, wherein said remedial component includes a stop member formed intermediate the ends thereof, said block includes a hole through which the other end of said remedial component projects such that said block engages said stop member when said remedial component is fixedly secured to said block.

9. A vertebral locking and retrieving system as claimed in claim 8, wherein the other end of said remedial component is threaded and said fastening means comprises at least one nut which is threadably received on said other end of said remedial component such that said block is sandwiched between said at least one nut and said stop member.

10. A vertebral locking and retrieving system as claimed in claim 1, wherein said remedial component comprises a second locking pin assembly.

* * * * *